US008921115B2

(12) United States Patent
Yuan et al.

(10) Patent No.: US 8,921,115 B2
(45) Date of Patent: Dec. 30, 2014

(54) APPARATUS AND METHOD FOR ANALYZING BLOOD CLOTTING

(71) Applicant: Medtronic, Inc., Minneapolis, MN (US)

(72) Inventors: Charlene Yuan, Brooklyn Park, MN (US); Trevor Huang, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/788,283

(22) Filed: Mar. 7, 2013

(65) Prior Publication Data

US 2014/0256052 A1    Sep. 11, 2014

(51) Int. Cl.
*G01N 33/86* (2006.01)
*G01N 33/48* (2006.01)

(52) U.S. Cl.
CPC ..................... *G01N 33/86* (2013.01)
USPC ............... 436/69; 436/63; 436/150; 422/73; 600/369

(58) Field of Classification Search
CPC ... G01N 33/48; G01N 33/49; G01N 33/4905; G01N 33/86; G01N 27/72; G01N 27/74
USPC ............ 436/63, 69, 149, 150; 422/68.1, 73; 435/13; 600/369; 73/64.41
See application file for complete search history.

(56) References Cited

U.S. PATENT DOCUMENTS

| | | | |
|---|---|---|---|
| 3,967,934 A * | 7/1976 | Seitz et al. | 422/73 |
| 4,752,449 A | 6/1988 | Jackson et al. | |
| 5,174,961 A | 12/1992 | Smith | |
| 5,314,826 A | 5/1994 | Baugh | |
| 5,441,892 A | 8/1995 | Baugh | |
| 5,629,209 A | 5/1997 | Braun, Sr. et al. | |
| 5,925,319 A | 7/1999 | Baugh et al. | |
| 5,951,951 A | 9/1999 | Lane et al. | |
| 6,010,911 A | 1/2000 | Baugh et al. | |
| 6,221,672 B1 | 4/2001 | Baugh et al. | |
| 6,541,262 B1 | 4/2003 | Baugh et al. | |
| 6,613,286 B2 | 9/2003 | Braun, Sr. et al. | |
| 6,613,573 B1 | 9/2003 | Cohen | |
| 7,399,637 B2 * | 7/2008 | Wright et al. | 436/69 |
| 7,422,905 B2 * | 9/2008 | Clague et al. | 436/69 |

(Continued)

FOREIGN PATENT DOCUMENTS

| | | |
|---|---|---|
| WO | WO97/41444 | 11/1997 |
| WO | WO00/40963 | 7/2000 |

(Continued)

OTHER PUBLICATIONS

Breet et al., Comparison of Platelet Function Tests in Predicting Clinical Outcome in Patients Undergoing Coronary Stent Implantation, JAMA, Feb. 24, 2010, vol. 303, No. 8.

(Continued)

*Primary Examiner* — Maureen Wallenhorst

(57) ABSTRACT

The invention includes systems, apparatuses and methods to evaluate the strength of clotting in addition to or separate from activated clotting time. The strength of clotting may be correlated with the amount of energy employed to move an object within blood. The strength of clotting may be correlated with the amount of time for fibrinolysis to occur. The strength of clotting may be determined by a system in which a ferromagnetic material is moved within blood.

24 Claims, 6 Drawing Sheets

(56) References Cited

U.S. PATENT DOCUMENTS

| | | | |
|---|---|---|---|
| 8,322,195 B2* | 12/2012 | Glauner et al. | 73/54.33 |
| 2007/0059840 A1* | 3/2007 | Cohen et al. | 436/69 |
| 2008/0268483 A1 | 10/2008 | Goldenberg et al. | |
| 2011/0104738 A1* | 5/2011 | Forsell | 435/29 |
| 2012/0329082 A1 | 12/2012 | Viola et al. | |

FOREIGN PATENT DOCUMENTS

| | | |
|---|---|---|
| WO | WO02/50535 | 6/2002 |
| WO | WO2005/106467 | 11/2005 |
| WO | WO2009/073851 | 6/2009 |
| WO | WO2009/123555 | 10/2009 |

OTHER PUBLICATIONS

Eikelboom et al., "Antiplatelet Drugs: Antithrombotic Therapy and Prevention of Thrombosis, 9th ed: American College of Chest Physicians Evidence-Based Clinical Practice Guidelines" Chest 2012; 141; e89S-e119S.

Gurbel et al., "Platelet Function Monitoring in Patients With Coronary Artery Disease" Journal of the American College of Cardiology, vol. 50, No. 19, 2007.

Hillman, Robert S. PhD "Letter to the Editor—Platelet Aspirin Resistance Detection and Validation" JACC, vol. 47, No. 12, 2006, Jun. 20, 2006: 2563-70.

Pakala et al., "Currently Available Methods for Platelet Function Analysis: Advantages and Disadvantages" Cardiovascular Revascularization Medicine 2010.

Picker, Susanne M. "In-Vitro Assessment of Platelet Function" Transfusion and Apheresis Science 44 (2011) 305-319.

Pittens et al., "Comparison Between Hirudin and Citrate in Monitoring the Inhibitory Effects of P2Y12 Receptor Antagonists With Different Platelet Function Test" Journal of Thrombosis and Haemostasis, 7: 1929-1949, 2009.

Weber et al., "A Point-of-Care Assessment of the Effects of Desmopressin on Impaired Platelet Function Using Multiple Electrode Whole-Blood Aggregometry in Patients After Cardiac Surgery" www.anesthesia-analgesia.org, Mar. 2010, vol. 110, No. 3.

PCT/US2014/020580, Partial International Search Report, mailed Jun. 26, 2014.

PCT/US2014/032774, PCT International Search Report and Written Opinion, mailed Jul. 17, 2014.

* cited by examiner

US 8,921,115 B2

APPARATUS AND METHOD FOR ANALYZING BLOOD CLOTTING

FIELD

This disclosure generally relates to, among other things, apparatuses and methods for detecting changes in a property of a fluid, such as clotting of blood.

BACKGROUND

A number of apparatuses for providing point-of-care analysis of blood clotting are available. These apparatuses are configured to provide valuable information regarding blood clotting, platelet function and bleeding complications. Such apparatuses are useful in a variety of circumstances such as before or during surgery to assist in determining or maintaining appropriate levels of anticoagulant therapy, or following therapy to determine blood status following discontinuation of anticoagulant therapy. However, additional or reconfigured apparatuses that provide for easy testing or additional information are desirable.

For example, easy, informative and accurate analysis of blood clotting and platelet function can be important for patients exhibiting abnormal bleeding post cardiopulmonary bypass. Although more than half of such patients exhibit abnormal bleeding due to incomplete surgical homeostasis, which is often corrected by exploration, a large number of such patients exhibit abnormal bleeding because of acquired platelet dysfunctions, consumptive coagulopathy, heparin rebound, protamine excess, primary fibrinolysis, etc. Accordingly, acquiring information regarding platelet function and bleeding complications could help to identify a cause of abnormal bleeding that is not a result of incomplete surgical hemostasis and reduce the reoperation rate.

SUMMARY

This disclosure describes, among other things, apparatuses and methods that provide for ready and informative evaluation of blood clotting status. In embodiments, the methods and apparatuses are configured to evaluate the strength of clotting in addition to or separate from activated clotting time. In embodiments, strength of clotting is correlated with amount of energy employed to move an object within blood. In embodiments, strength of clotting is correlated with amount of time for fibrinolysis to occur. In embodiments, strength of clotting is determined by a system in which a ferromagnetic material is moved within blood.

In embodiments, systems, apparatuses and methods described herein correlate the amount of energy employed to move an object in blood to clot strength. Movement of the object may also be monitored and used in combination with energy input to further enhance determinations of clot strength in various embodiments.

In an aspect, a method carried out by an apparatus or system configured to analyze blood clotting includes expending energy to cause, or attempt to cause, an object to move in a chamber housing blood; and correlating the amount of energy expended with the strength of clotting of the blood. The method may further include detecting the rate of movement of the object in the chamber and correlating the rate of detected movement of the object with the clotting strength of the blood.

In an aspect, a method carried out by an apparatus or system configured to analyze blood clotting includes:

(a) applying energy configured to cause an object to move in a chamber housing blood;
(b) detecting movement of the object in the chamber during or after the application of the energy;
(c) determining whether the detected movement of the object meets or exceeds a predetermined threshold;
(d) applying additional energy configured to cause the object to move if the detected movement of the object is determined not to meet or exceed the threshold in step (c);
(e) repeating steps (c) and (d) until the detected movement of the object is determined to meet or exceed the predetermined threshold or until a predetermined energy threshold is met or exceeded; and
(f) correlating the amount of energy applied to attempt to cause, or cause, the object to move with the strength of the clot.

In embodiments, systems, apparatuses and methods described herein correlate the time for fibrinolysis to occur with clot strength. Fibrinolysis may be determined in any suitable manner. For example, fibrinolysis may be determined by determining whether an object in blood moves more freely relative to the movement of the object in the blood at a time when the blood was determined to be clotted. Alternative, thresholds of rate of movement of an object in the blood, or the like, may be used to determine whether fibrinolysis has occurred.

In an aspect, a method carried out by an apparatus or system configured to analyze blood clotting includes:

(a) determining whether blood has clotted in a chamber housing the blood and identifying time at which the blood has determined to have clotted;
(b) attempting (e.g., in the form of lifting power, i.e. energy) to cause an object to move in a chamber housing blood at a predetermined time (e.g., during a test cycle) after the blood has been determined to be clotted;
(c) detecting movement (e.g., distance or velocity) of the object in the chamber after attempting to cause the object to move;
(d) determining whether the detected movement of the object meets or exceeds a predetermined threshold (e.g., for distance or velocity);
(e) attempting to cause the object to move in the chamber housing the blood at a subsequent predetermined time (e.g., in the next or subsequent test cycle) if the detected movement of the object is determined to not meet or exceed the threshold in step (d);
(f) repeating steps (d) and (e) until the detected movement of the object is determined to meet or exceed the predetermined threshold;
(f) determining the length of time from the time at which the blood had been determined to have clotted until the detected movement of the object is determined to meet or exceed the predetermined threshold; and
(g) correlating the length of time determined in step (f) to the strength of the clot.

In an aspect, a method carried out by an apparatus or system configured to analyze blood clotting includes causing an object to move in a chamber housing blood; detecting movement of the object in the chamber in a period of time and detecting movement of the object in the chamber in a second period of time; and determining whether the detected movement of the object in the first period of time is indicative of clotting. The method further includes determining whether the detected movement of the object in the second period of time is greater than the detected movement in the first period of time at the time clot was detected; determining elapsed time between the first period of time and the second period of time; and correlating strength of blood clotting to the length of the elapsed time if the detected movement of the object in the first period of time is determined to be indicative of clotting and if the detected movement of the object in the second period of time is determined to be greater than the detected movement in the first period of time at the time clot was detected.

In an aspect, a method carried out by an apparatus or system configured to analyze blood clotting includes causing an object to move in a chamber housing blood; detecting movement of the object in the chamber in a first period of time and detecting movement of the object in the chamber in a second period of time; and determining whether the detected movement of the object in the first period of time is indicative of clotting. The method further includes determining whether the detected movement of the object in the second period of time is indicative of clot weakening; determining elapsed time between the first period of time and the second time; and correlating strength of blood clotting to the length of the elapsed time if the detected movement of the object in the first period of time is determined to be indicative of clotting and if the detected movement of the object in the second period of time is indicative of clot weakening.

In embodiments, systems, apparatuses and methods described herein employ a ferromagnetic object moved within blood by activation of a magnet to determine strength of clotting. Existing systems that employ such ferromagnetic objects are readily available for point-of-care blood analysis and may be readily modified to carry out the methods described herein. In embodiments, systems, apparatuses and methods described herein control the rate of movement of a ferromagnetic object in blood due to activation of a magnet to provide nuanced information regarding clot strength.

In an aspect, a method carried out by an apparatus or system configured to analyze blood clotting includes causing a ferromagnetic object to move in a chamber housing blood after the blood has been determined to have clotted; detecting of movement of the ferromagnetic object in the chamber; and correlating the detected movement of the ferromagnetic object in the chamber with strength of clotting of the blood.

In an aspect, a method carried out by an apparatus or system configured to analyze blood clotting includes:
(a) inputting energy to cause a ferromagnetic object to move in a chamber housing blood;
(b) detecting movement of the ferromagnetic object in the chamber and determining the initial object travel distance or velocity;
(c) determining whether the detected movement of the ferromagnetic meets a predetermined ferromagnetic object travel distance threshold (e.g., a distance is less than the initial distance) or velocity threshold (e.g., a velocity less than initial velocity) for clot formation;
(d) inputting increased energy relative to step (a) to cause the ferromagnetic object to move the initial travel distance or velocity; and
(e) repeating steps (c)-(d) until the detected movement of the ferromagnetic object in the chamber meets the predetermined ferromagnetic object travel distance or velocity threshold for clotting or until a predetermined energy threshold is met or exceeded.
The reduced movement of the object or increased energy to move the object corresponds to clot formation, while the energy difference between start and time at clotting is indicative of clot strength. At this point, the coagulation process of the blood should complete or near complete. The method may further include fibrinolysis analysis. For example, the method may further include the following steps:

(f) applying energy to cause the ferromagnetic object to move or attempt to move at a level of energy applied at step (e);
(g) detecting movement of the ferromagnetic object in the chamber;
(h) determining whether the detected movement of the first ferromagnetic meets a predetermined ferromagnetic threshold for clot weakening;
(i) repeating steps (f)-(h) until the detected movement of the ferromagnetic meets the predetermined ferromagnetic threshold for clot weakening;
(j) inputting decreased energy relative to step (e) to cause the ferromagnetic object to move or attempt to cause the ferromagnetic object to move in the chamber;
(k) detecting movement of the ferromagnetic object in the chamber;
(l) determining whether the detected movement of the ferromagnetic object returns to the initial object travel distance or velocity;
(m) inputting energy at the same level as input in step (i) to cause the ferromagnetic object to move or attempt to cause the ferromagnetic object to move in the chamber if the detected movement of the ferromagnetic object does not return to the initial object travel distance or velocity; and
(n) repeating step (j) to (m) until energy is reduced to the test initial level.
At this point, the fibrinolysis process should be complete.

One or more embodiments of the apparatuses, systems or methods described herein provide one or more advantages over prior apparatuses, systems or methods for evaluating a change in a property of a liquid, such as clotting of blood. For example, the apparatuses, systems and methods described herein provide for more direct measurement of clot strength or alternative measurements of clot strength; each of which provides advantages or diversity to the important area of blood analysis. These and other advantages will be readily understood from the following detailed description.

Figure 1:
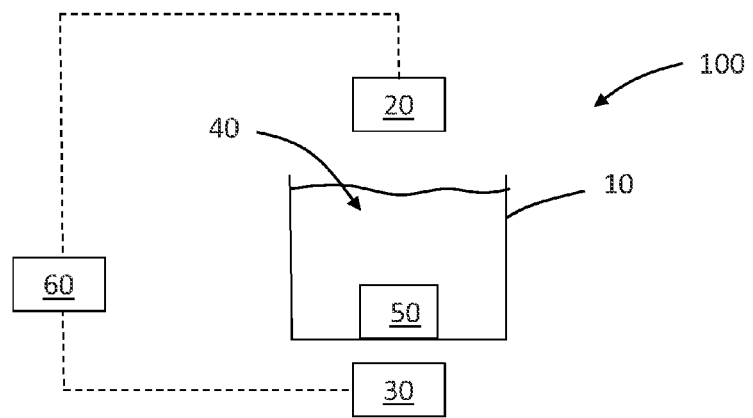
FIG. 1 is a schematic drawing of selected components of an embodiment of a blood analysis system.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description several specific embodiments of compounds, compositions, products and methods are disclosed. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. As used herein, "consisting essentially of," as it relates to an composition, product, method or the like, means that the components of the composition, product, method or the like are limited to the enumerated components and any other components that do not materially affect the basic and novel characteristic(s) of the composition, product, method or the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

As used herein, determining or correlating "strength of clotting" means performing a calculation or estimation that employs a parameter indicative of clotting that occurs after activating clotting time or initiation of clot formation to determine or correlate the parameter to the strength of the clot.

Any direction referred to herein, such as "top," "bottom," "left," "right," "upper," "lower," and other directions and orientations are described herein for clarity in reference to the figures and are not to be limiting of an actual device or system or use of the device or system. Devices or systems as described herein may be used in a number of directions and orientations.

As used herein, a clot is determined to be "fully formed" when an object disposed in blood moves a distance or velocity that is lower than a predetermined distance or velocity or when energy configured to cause the object to move within the blood exceeds a predetermined threshold without moving the object to a predetermined distance or rate.

As used herein, a "predetermined" threshold value is a value that is determined prior to the time in which it is compared to another value. The value may be based on baseline data obtained earlier in time than the value to which it is being compared, may be a value placed in memory prior to analysis, or the like.

This disclosure generally relates to, inter alia, apparatuses and methods for detecting changes in a property of a fluid, such as clotting of blood. In particular, apparatuses, systems and methods described herein, among other things, provide for ready and informative evaluation of blood clotting status. In embodiments, the methods and apparatuses are configured to evaluate the strength of clotting in addition to or separate from activated clotting time. In embodiments, strength of clotting is correlated with amount of energy employed to move an object within blood. In embodiments, strength of clotting is correlated with amount of time for fibrinolysis to occur. In embodiments, strength of clotting is determined by a system in which a ferromagnetic material is moved within blood.

In embodiments, the methods described herein are employed by, or the systems described herein include, any suitable apparatus for analyzing blood clotting. For example, plunger-type systems or apparatuses such as those described in U.S. Pat. Nos. 6,010,911; 5,174,961; 4,752,449; 5,951,951; 5,925,319; 5,314,826; and 5,541,892; systems or apparatuses that employ ferromagnetic particles moved by electromagnets such as those described in U.S. Pat. Nos. 5,626,209 and 6,613,286; or the like may be employed in accordance with the teaching presented herein or may be modified to perform the methods described herein. Each of the afore-mentioned patents is hereby incorporated by reference in their respective entirety to the extent that it does not conflict with the disclosure presented herein. In aspects, the description presented herein is tailored to systems and apparatuses that employ ferromagnetic particles moved by electromagnets. However, it should be understood that other suitable systems and apparatuses, in many cases, may be used to carry out the methods described herein.

Regardless of the type of system employed, a blood clotting analysis system includes a chamber or container into which blood may be placed for analysis. The system is typically configured to mix the blood with one or more substance that may affect clotting of the blood. For example, the system may employ sonic, ultrasonic or other waves, washers, plungers, rods, shaking, or the like to mix the blood and one or more substances. The substances or agitation of blood may facilitate clotting of the blood. The system is configured to monitor changes in blood viscosity and correlate such changes with clotting status. For example, the system may include one or more detectors for monitoring waves, monitoring position or rate of movement of an object such as a plunger or washer, monitoring relative phase of a rod, or the like to determine whether blood viscosity or clotting status has changed. Typically, the system is configured to determine the amount of time for blood clotting to occur, which is often referred to as activated clotting time. The system may include more than one chamber configured to contain blood and different agents that affect clotting so that comparisons of activating clotting time in the various chambers can be used to derive information regarding the blood clotting process.

Figure 2:
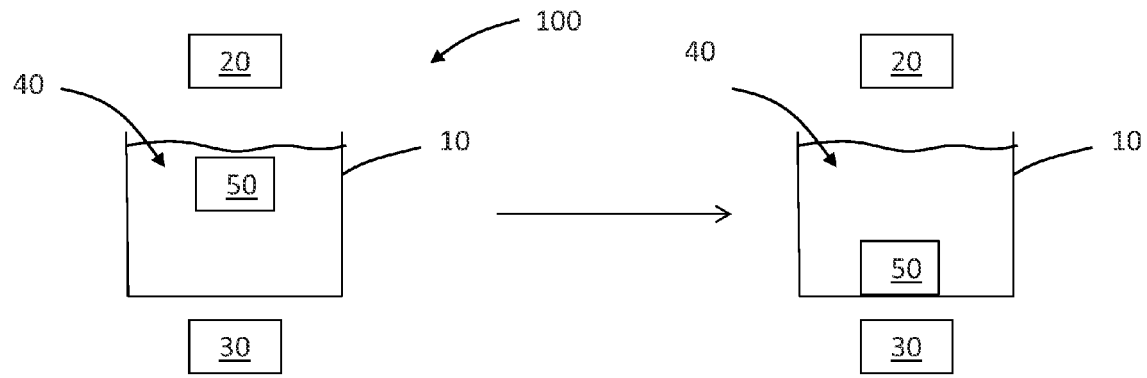
FIG. 2 is a schematic drawing of selected components of an embodiment of a blood analysis system showing an object moveable within a chamber containing blood.

By way of example and with reference to FIGS. 1-2, schematic drawings of selected components of an example of a blood analysis system 100 are shown. The depicted system 100 is a system that employs a ferromagnetic object 50 moveable within blood 40 contained within chamber 10. In embodiments, the chamber is configured to remain stationary during the testing process. The object 50 is moveable against gravity by electromagnet 20, which is operably coupled to electronics 60 (see, FIG. 2, left). Electronics 60 are configured to control activation of electromagnet 20. The object 50 may be moved against gravity and the position or rate of movement of the object 50 within the chamber 10 as object 50 falls through blood 40 may be detected by sensor 30 (see, FIG. 2, right), which is also operably coupled to electronics 60.

Electronics 60 may include a processor, memory, user interface, timer or counter, powers source or the like. Electronics may include any suitable processor, such as one or more microprocessors, DSPs, ASICs, FPGAs, programmable logic circuitry, or the like, and the functions attributed to the processor herein may be embodied as hardware, firmware, software or any combination thereof. Memory may store instructions that cause processor to provide the functionality ascribed to a system or apparatus described herein, and may store information used by processor to provide the functionality ascribed to a system or apparatus described herein. Memory may include any fixed or removable magnetic, optical, or electrical media, such as RAM, ROM, CD-ROM, hard or floppy magnetic disks, EEPROM, or the like. Memory may also include a removable memory portion that may be used to provide memory updates or increases in memory capacities. A power source may deliver operating power to components of a system or apparatus described herein. Power source may be an AC or DC power source, such as a battery and a power generation circuit to produce the operating power.

Still with reference to FIGS. 1-2, as blood 40 viscosity increases, such as when the blood clots, the rate of movement of object 50 falling through blood 40 will decrease. Electronics 60, based on data from sensor, are configured to determine the distance the object 50 falls or the velocity at which the object 50 falls. Electronics 60 may be configured to detect activated clotting times by, for example, determining when distance or velocity decreases by a predetermined amount or percent relative to an initial distance or velocity. As discussed above, additional details regarding such types of blood clotting analysis apparatuses and systems are described in, for example, U.S. Pat. Nos. 5,626,209 and 6,613,286.

Unlike such previously described systems and apparatuses employing a moveable ferromagnetic object 50, such as a washer, the systems and apparatuses described herein are configured to evaluate the strength of clotting in addition to or alternatively to activated clotting time. Additional detail regarding embodiments of methods that may be employed by such systems and apparatuses will be discussed below.

Figure 3:
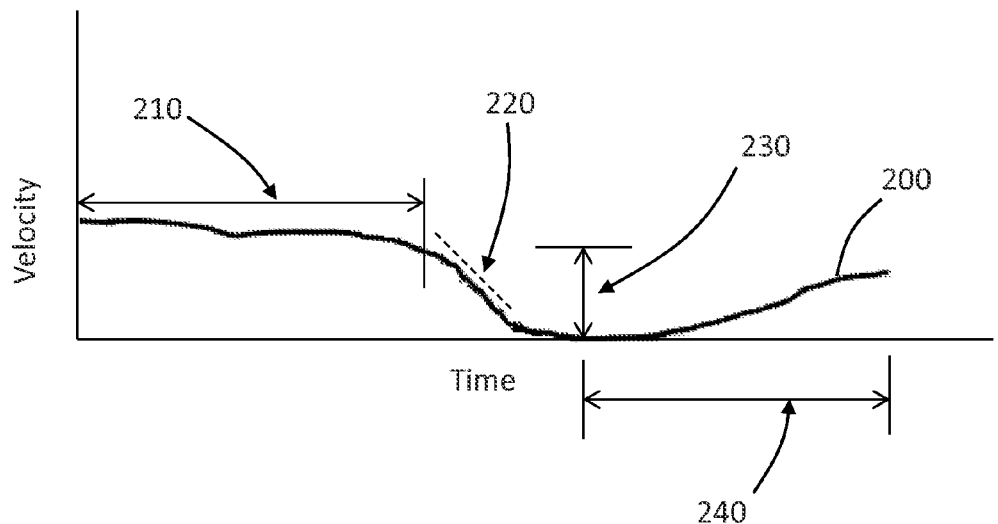
FIG. 3 is a schematic drawing of a predicted trace of velocity of an object over time that may be representative of data obtainable by an embodiment of a blood analysis apparatus.

Referring now to FIG. 3, a schematic drawing is shown of a predicted trace 200 of velocity of an object (e.g., ferromagnetic object 50 as depicted in, and described with regard to, FIGS. 1-2) over time that may be representative of data obtainable by an embodiment of a blood analysis apparatus or system. The depicted trace 200 illustrates data predicted to be obtained during coagulation (to the left of trough in trace 200) and fibrinolysis (to the right of the trough in trace 200) processes. Before the blood begins to coagulate, the velocity at which the object falls through the blood remains fairly constant (see left most portion of trace 200). However, as the blood begins to coagulate and clot, the velocity at which the object falls through the blood begins to decrease. The time at which velocity decreases by a certain percentage or amount of baseline or initial velocity is used to calculate activated clotting time 210. However, if additional cycles of testing or analysis are performed (e.g., the object is raised against gravity and the velocity of the object falling is monitored) after activated clotting time 210 is determined, additional information regarding clot strength can be obtained. As shown, the velocity of the object is predicted to continue to decrease until the blood reaches maximum viscosity (e.g., the blood has fully coagulated or fully clotted—represented by trough in trace 200). In many circumstances, the object will not move (e.g., lifted up or fall down) because the viscosity of the blood is too great. In some cases, the object may become trapped within a clot. The minimum velocity of the object, which may represent fully coagulated or clotted blood, may be used in determining clot strength. As depicted in FIG. 3, the slope 220 of the portion of trace 200 (or rate of change in velocity following activated clotting) indicative of clotting may be used to determine relative strength of clotting, with larger magnitude slopes 220 (greater rates of change) being predicted to be indicative of stronger clotting. In addition or alternatively, the magnitude of the change in velocity 230 of the object through the blood from the initial or baseline velocity to the minimum velocity may be used to determine the relative strength of the clot, with a larger magnitude 230 being predicted to be indicative of stronger clots.

As shown in FIG. 3, with particular reference to the portion of trace 200 to the right of the trough, after a period of time of rest or of minimal disturbance of the blood the clot will begin to lyse, the blood will become less viscous, and the velocity at which the object will move through the blood will increase. The time at which the velocity of the object increases a certain amount or percentage from the minimum velocity may be used to determine lysis time 240.

Figure 4:
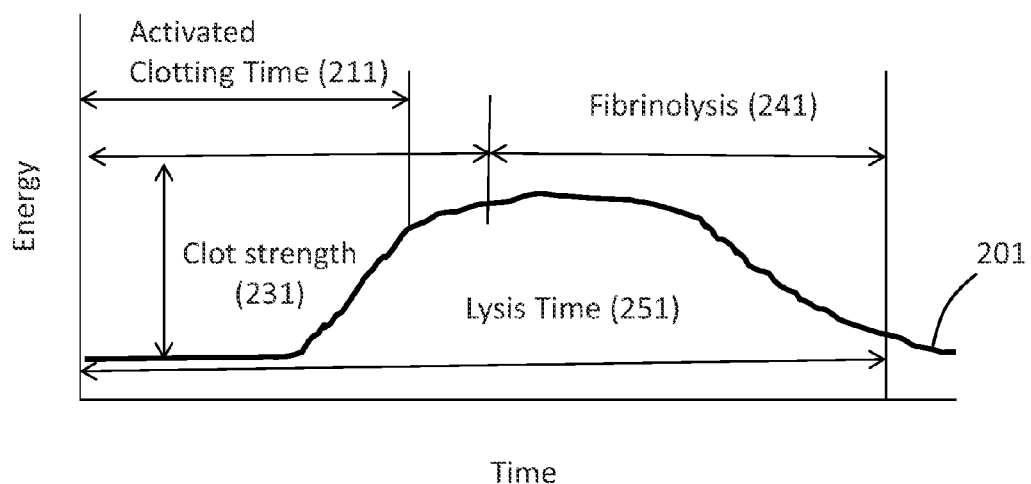
FIG. 4 is a schematic diagram of a predicted trace of energy input to cause an object to move in blood over time that may be representative of data obtainable by an embodiment of a blood analysis apparatus.

Referring now to FIG. 4, a schematic drawing is shown of a predicted trace 201 of energy input to cause (or attempt to cause) of an object (e.g., ferromagnetic object 50 as depicted in, and described with regard to, FIGS. 1-2) over time that may be representative of data obtainable by an embodiment of a blood analysis apparatus or system. The depicted trace 201 illustrates data predicted to be obtained during coagulation (to the left of peak in trace 201) and fibrinolysis (to the right of the peak in trace 201) processes. Before the blood begins to coagulate, the energy required to cause the object to move through the blood remains fairly constant (see left most portion of trace 201). However, as the blood begins to coagulate and clot, the energy required to cause the object to move through the blood begins to increase (assuming the object is trapped in or below the clot and the energy is configured to cause the object to rise). The time at which the energy requirement increases by a certain percentage or amount of baseline or initial energy may be used to calculate activated clotting time 211. As shown, the energy needed to cause the object to move is predicted to continue to increase until the blood reaches maximum viscosity (e.g., the blood has fully coagulated or fully clotted—represented by peak in trace 201). In many circumstances, the object will not move (e.g., lifted up or fall down) because the viscosity of the blood is too great. The maximum energy used to cause (or attempt to cause) the object to move, which may represent fully coagulated or clotted blood, may be used in determining clot strength (231).

As shown in FIG. 4, with particular reference to the portion of trace 201 to the right of the peak, after a period of time of rest or of minimal disturbance of the blood the clot will begin to lyse, the blood will become less viscous, and the amount of energy needed to cause the object to move through the blood will decrease. The time at which the input energy needed to move the object decreased a certain amount or percentage from the maximum energy may be used to determine fibrinolysis time 241 or lysis time 251.

Figure 5:
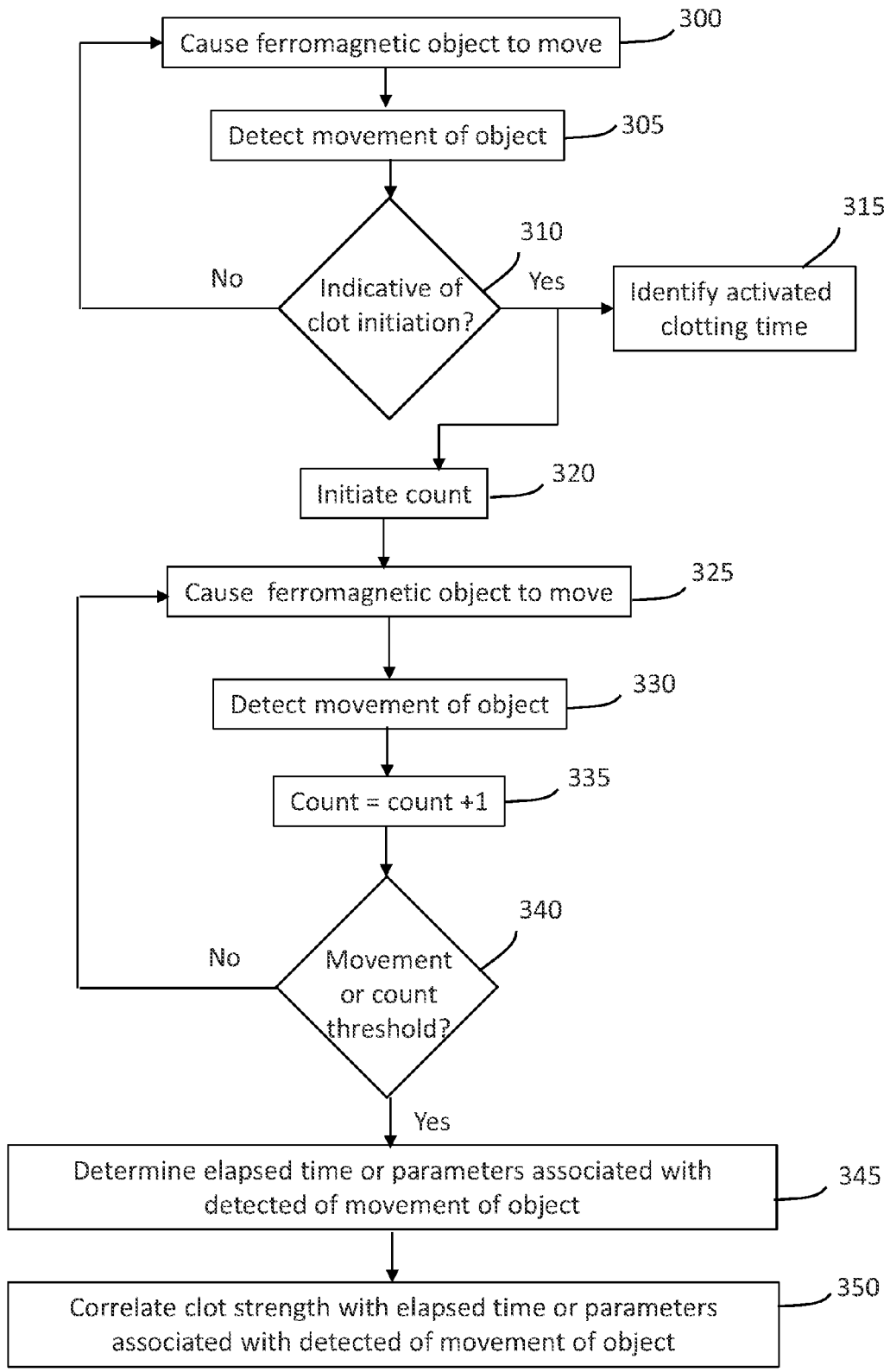
FIGS. 5-7 are flow diagrams of embodiments of methods described herein.
Figure 6:
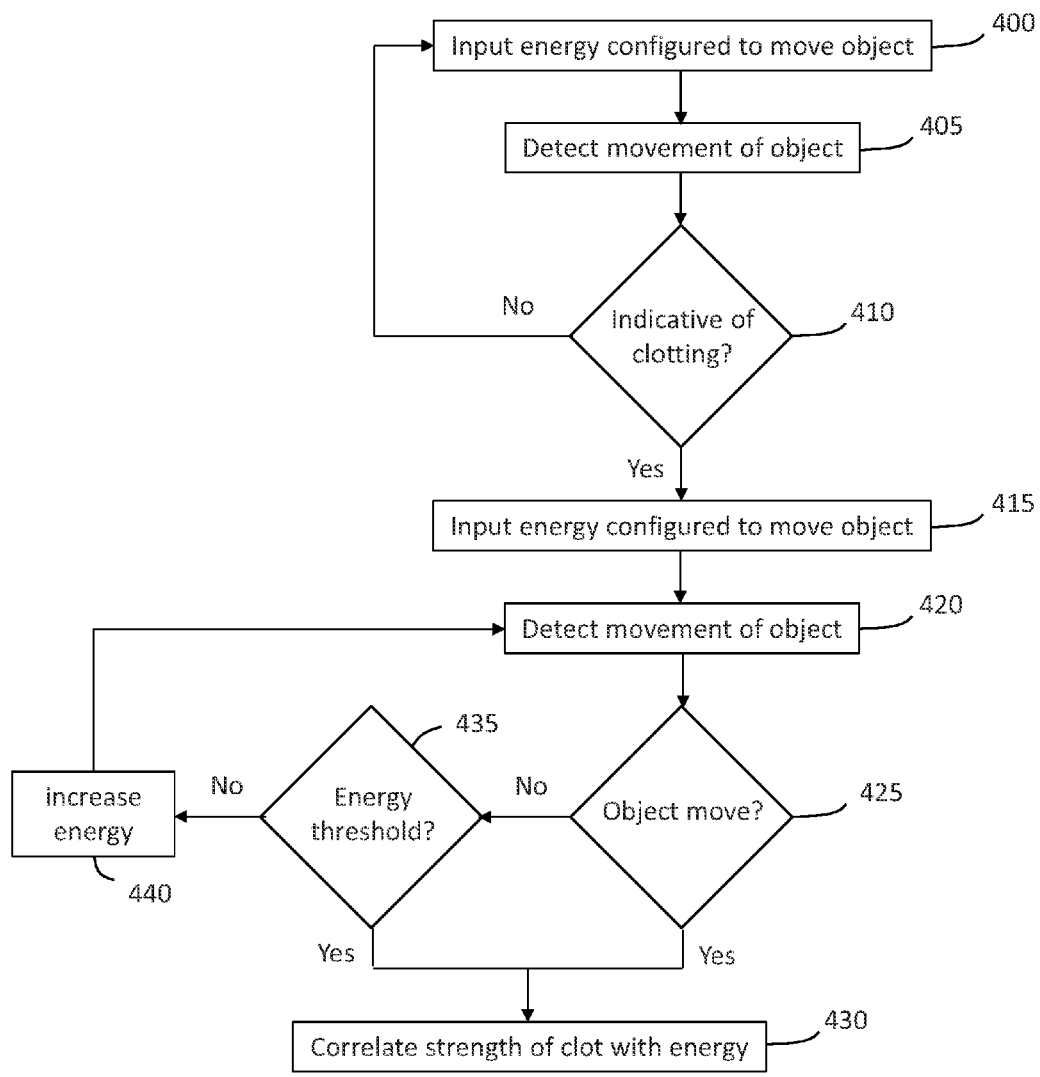
Figure 7:
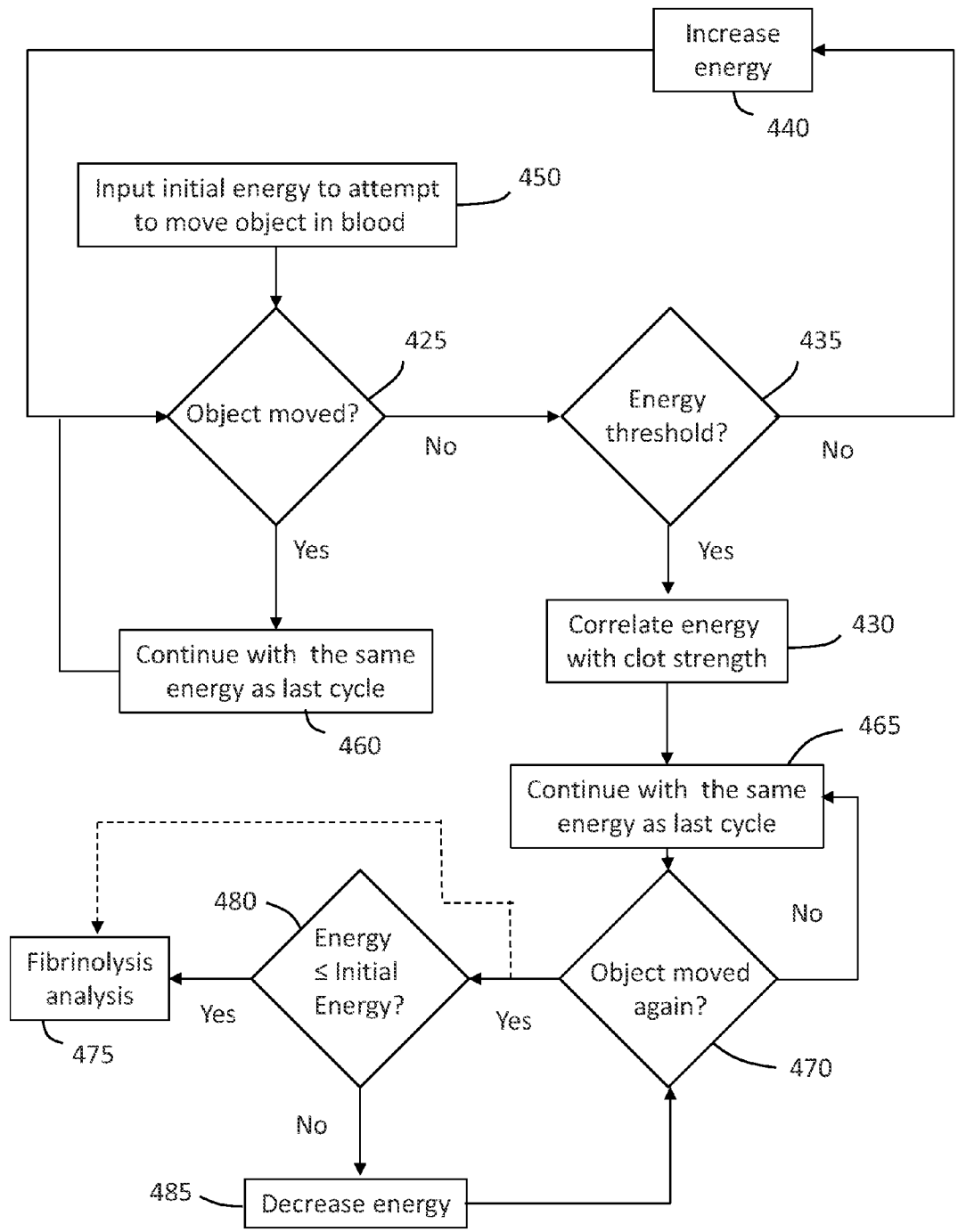

Described below in FIGS. 5-7 are flow diagrams of methods that may be employed by apparatuses or systems to analyze blood clot strength. The methods may be carried out by apparatuses or systems that employ ferromagnetic objects that are moved through blood via an electromagnet. However, it will be understood that embodiments of the methods described below may be carried out by other types of blood analysis apparatuses or systems, such as those that employ plungers or rods. The methods described below may be better understood with reference to FIGS. 3-4 above. In embodiments, clot strength is correlated to rate of change of movement of an object through blood (e.g, slope 220 in FIG. 3) or magnitude of change in movement (e.g., magnitude 230 in FIG. 3). In embodiments, lysis time (element 240 in FIG. 3) or amount of energy require to break an object free from a clot are used to determine clot strength (see, e.g., FIG. 4). The use of energy use as a factor in determining clot strength is also described in embodiments below.

Referring now to FIG. 5, an overview of a method for determining clot strength is depicted. The method includes causing an object, such as a ferromagnetic object, to move in a chamber housing blood (300); e.g., by activating an electromagnet, and detecting the rate of movement of the object through blood in the chamber (305), such as the object rising or falling through the blood. The method further includes determining whether the position or velocity of the object is indicative of clot initiation (310), which can be determined by, for example, determining whether movement has declined a predetermined amount or percentage relative to baseline or has decreased below a threshold value that has been determined to be indicative of clot initiation. If the detected movement of the object is determined to be indicative of clot initiation, activated clot time may be calculated (315); e.g., by determining the length of time from start to clot initiation. Clot strength may then be determined with further cycles of testing.

As illustrated in FIG. 5, the method further includes initiating a counter or timer (320) and causing an object, such as a ferromagnetic object, to move to in the chamber housing blood (325); e.g., by activating an electromagnet. The rate of movement of the object through blood in the chamber is then detected (330), such as the object falling through the blood, and the counter or timer is increased (335). The process is repeated until ferromagnetic object movement (e.g., indicated by travel distance or velocity) threshold or count threshold has been reached (340). The cyclic process of moving the object through the blood and determining the rate of falling of the object may be ceased if either threshold is reached, and a parameter associated with the detected movement of the object may be calculated or determined (345). The parameter may be, for example, the slope or rate of change in velocity or the magnitude in change in velocity. Clot strength is then correlated with the parameter (350).

Referring now to FIG. 6, a method for determining clot strength associated with energy input required to move an object through blood is depicted. In the depicted embodiment, energy configured to move the object is input (400), such as activation of an electromagnet to cause a ferromagnetic object to move, and the movement of the object is detected (405). The movement may be detected during or after the application of energy (400). For example, movement of the object against gravity (e.g., while energy is applied) or falling (e.g., after energy is applied) may be detected. A determination may be made as to whether movement of the object is indicative of clotting (410). If determination is made that movement of the object is not indicative of the predetermined clot indicating threshold, the process may be repeated as depicted until the predetermined clot indicating threshold has been determined to have been reached.

Energy configured to move the object again is then input (415), which may be more or less than previously input energy, and movement of the object is detected (420). In embodiments, the energy input at step 415 is intentionally low and may not cause the object to move (or to move a predetermined rate or distance). A determination is then made as to whether the object had moved (425). This determination may be a determination as to whether the object move any substantial amount, whether the rate or distance of movement of the object met or exceeded a predetermined threshold, or the like.

If the object is determined not to have moved or to have moved a distance or rate below a predetermined threshold, a determination is made as to whether an energy threshold has been reached is made (435). If the energy threshold is not reached, the input energy is increased (440) and movement of the object is detected (420). This process is repeated as depicted until it is determined that the object has moved a predetermined distance or velocity (425) or until the energy threshold has been reached (435). The strength of the clot is then correlated with the amount of energy input to cause, or attempt to cause, the object to move.

In FIG. 7, the amount of energy it takes to move an object in not clotted and clotted blood samples is determined. The method depicted in FIG. 7 omits some steps depicted in FIG. 6, such as detecting movement of the object, but is should be understood that such steps may be applied with the method depicted in FIG. 7 as needed or desired.

The method depicted in FIG. 7 includes inputting energy to attempt to move an object in blood that has not clotted (450). A determination is made as to whether the object has moved (425), such as described above with regard to FIG. 6. If the object is determined to have moved or moved greater than a pre-determined threshold, the process is repeated with the same energy as the last cycle (460). If the object is determined not to have moved or moved less than the pre-determined threshold, a determination is made as to whether an energy threshold has been reached (435). If the energy threshold has not been reached, the amount of energy input to attempt to cause the object to move is increased (440). The process is repeated as depicted until the object is determined to have not moved (425) (or has moved a distance or rate below the predetermined threshold) or until the energy threshold is reached (435). Once the energy threshold has been reached and the object has not moved, a clot is considered to be formed. The clot strength is then correlated with the amount of energy input to move the object or to attempt to move the object (430). Activated clotting time, etc. may also be determined (e.g., as discussed above with regard to FIG. 6).

Still with reference to FIG. 7, after the clot is indicated, fibrinolysis analysis may be conducted. As shown at step 465, energy is input to attempt to cause the object to move, where the energy input is the same the cycle in which clotting was determined (energy threshold met and object did not move above threshold value), and a determination is made as to whether the object has moved again (470). If the object is not moved or moves less than a pre-determined threshold distance or rate, the cycles are continued at the same energy as the previous cycle (470) until object is moved or moves greater than a pre-determined threshold. Fibrinolysis analysis (475) may be performed, such as based on elapsed time or the like. While not shown in FIG. 7, it will be understood that a counter or timer may be employed for determining fibrinolysis time or other aspects relating to clotting or for purposes of determining whether the system has timed out.

Alternatively or in addition, further data may be collected to aid in fibrinolysis analysis. Still with reference to FIG. 7, if the object is moved or moves greater than the pre-determined threshold (470), a determination is made as to whether the energy used was less than the initial energy used before blood clotting (energy used at step 450). If the initial energy (450)

has not yet been reached, the energy to cause the object move is decreased (485) and the process (steps 465 and 470) is repeated until the object is determined to move greater than the predetermined distance or velocity (470). The process (steps 480, 485, 465, 470) is repeated until the initial energy (450) has been reached (480). Fibrinolysis analysis (lysis time, etc.) may then be performed (475).

The methods depicted in FIGS. 5-7 are merely illustrative of the methods contemplated herein. It will be understood that other similar methods are contemplated and are encompassed by the spirit of this disclosure. It will be further understood that the methods presented in FIGS. 5-7 are not intended to be mutually exclusive and that one or more steps depicted and described herein within one or more of FIGS. 5-7 may be incorporated into other methods depicted and described herein with regard to one or more FIGS. 5-7.

It will be further understood that, while the methods depicted and described with regard to FIGS. 5-7 are discussed herein with regard to detection of movement of an object within a given chamber, the methods may be employed with regard to systems and apparatuses that use more than one such object and more than one such chamber.

In an example of a two chamber system, the first chamber may be used to indicate clot formation and determining activated clotting time, and a second chamber with a similar mechanical configuration and chemical composition as the first chamber may be used for clot strength determination or fibrinolysis test. While the first ferromagnetic object is caused to move in the first chamber for clot detection, the ferromagnetic object in the 2nd chamber rests at the bottom of the chamber. Once a clot is determined to have been initiated in the first chamber, the ferromagnetic object in the second chamber may then be caused to move as a result of input energy outlined in FIGS. 5-7 for clot strength determination or fibrinolysis analysis. The two chamber system ensures that the object is located at the bottom of the chamber at the time of clot formation in the second chamber, which allows magnetic force from the top of the chamber to lift the ferromagnetic object up for clot strength measurement. In circumstances in which a clot is formed at the bottom of the chamber and the ferromagnetic object is not trapped inside of or under the clot, the lifting energy on from the top of the chamber would move the object without perturbation of the clot, thus the clot strength may not be able to be accurately determined until clot is dissolved and washer moved to the bottom of the chamber via gravity.

Figure 8:
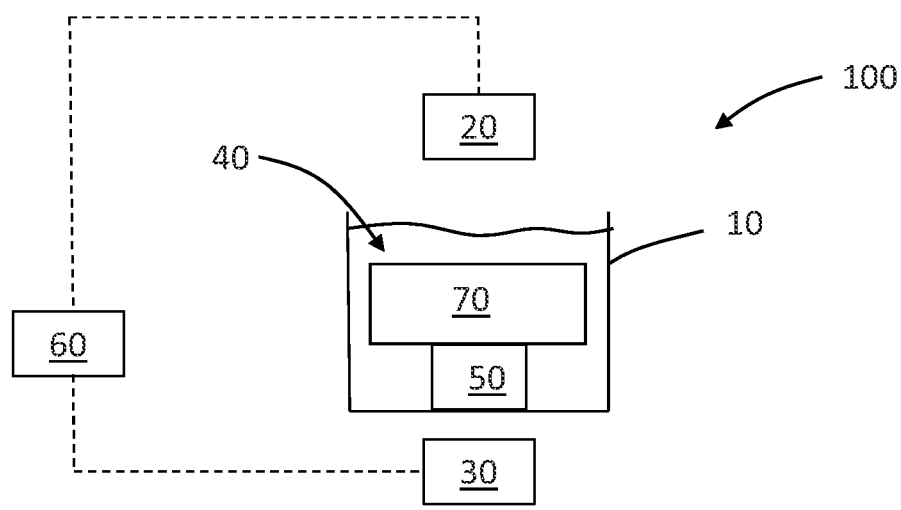
FIG. 8 is a schematic drawing of selected components of an embodiment of a blood analysis system showing an object moveable within a chamber containing blood.

An example of a single chamber system is depicted in FIG. 8, which shares may similar parts or components with those depicted in FIGS. 1-2. Like numbered parts or components are the same or similar between FIG. 8 and FIGS. 1-2. As these parts or components have been previously discussed above with regard to FIGS. 1-2, FIG. 8 will be discussed briefly with an emphasis on the differences. As shown in FIG. 8, the system 100 includes a spacer of elastic nature (e.g., a biasing member 70) that is inserted between the ferromagnetic object 50 and the magnet 20 on the top of, or above, the chamber 10. The elastic spacer or biasing member 70 is configured and positioned to pull or push down the object to ensure a clot is formed on top of the object or surrounds the object. With the clot on top or around washer, the clot can be perturbed by the object lifting and falling movement of the object 50, from which, the clot strength can be determined. Any suitable elastic spacer 70 may be used, such as a hemocompatible metal or polymeric spring.

Data regarding activated clotting time, clot strength, fibrinolysis, etc. obtained from a given chamber having one or more agents that affect blood clotting may be compared with similar data obtained from another chamber in which different agents are mixed with blood.

Methods described in this disclosure, including those attributed to apparatuses or systems, or various constituent components, may be implemented, at least in part, in hardware, software, firmware or any combination thereof. For example, various aspects of the methods may be implemented within one or more processors, including one or more microprocessors, DSPs, ASICs, FPGAs, or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry.

Such hardware, software, firmware may be implemented within the same apparatus or within separate apparatuses to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, apparatuses and methods described in this disclosure may be embodied as instructions on a computer-readable medium such as RAM, ROM, NVRAM, EEPROM, FLASH memory, magnetic data storage media, optical data storage media, or the like. Such computer-readable medium is non-transitory. The instructions may be executed by one or more processors to support one or more aspects of the functionality described in this disclosure.

A number of embodiments of methods, apparatuses, and systems are described herein. A summary of selected aspects of methods, devices and systems described herein is provided below.

In a first aspect, a method carried out by a system configured to analyze blood clotting, includes: (i) causing an ferromagnetic object to move in a chamber housing blood after clot initiation has been detected; (ii) detecting movement of the ferromagnetic object in the chamber; and (iii) correlating the detected movement of the ferromagnetic object in the chamber with strength of clotting of the blood.

A second aspect is a method of the first aspect, wherein causing the object to move in the chamber comprises causing the object to move in the chamber against the force of gravity, and wherein detecting movement of the object in the chamber comprises detecting movement of the object due to the force of gravity.

A third aspect is a method of the first aspect, wherein causing the object to move in the chamber comprises causing the object to move in the chamber against the force of gravity, and wherein detecting movement of the object in the chamber comprises detecting movement of the object against the force of gravity.

A fourth aspect is a method of any of aspects 1-3, wherein detecting movement of the first object in the first chamber comprises detecting movement in a first period of time and detecting movement in a second period of time, and wherein correlating detected movement of the object in the chamber with the strength of clotting comprises comparing movement of the object in the chamber in the first period of time to movement of the object in the chamber in the second period of time.

A fifth aspect is a method of the fourth aspect, wherein correlating movement of the object in the chamber with the strength of clotting comprises determining a rate of change in velocity of the object between the first period of time and the second period of time and correlating the rate of change in velocity with the strength of clotting.

A sixth aspect is a method of the fourth or fifth aspects, wherein correlating movement of the object in the chamber with the strength of clotting comprises determining a magnitude in the difference between movement of the object in the chamber in the first period of time and movement of the object in the chamber in the second period of time and correlating the magnitude with the strength of clotting.

A seventh aspect is a method of any of aspects 1-6, further comprising detecting clot initiation.

An eighth aspect is a method of the seventh aspect, wherein detecting clot initiation comprises: (i) causing the ferromagnetic object to move in the chamber housing the blood; (ii) detecting movement of the ferromagnetic object in the chamber; and (iii) determining whether the detected movement has decreased below a predetermined threshold, wherein, if the detected movement has decreased below the predetermined threshold, clot initiation is detected.

A ninth aspect is a method carried out by an apparatus or system configured to analyze blood clotting, comprising: (a) inputting energy to cause a ferromagnetic object to move in a chamber housing blood; (b) detecting movement of the ferromagnetic object in the chamber and determining the initial object travel distance or velocity; (c) determining whether the detected movement of the ferromagnetic meets a predetermined ferromagnetic object travel distance threshold or velocity threshold for clot formation; (d) inputting increased energy relative to step (a) to cause the ferromagnetic object to move the initial travel distance or velocity; and (e) repeating steps (c)-(d) until the detected movement of the ferromagnetic object in the chamber meets the predetermined ferromagnetic object travel distance or velocity threshold for clotting or until a predetermined energy threshold is met or exceeded.

A tenth aspect is a method of the ninth aspect, further comprising: (f) applying energy to cause the ferromagnetic object to move or attempt to move at a level of energy applied at step (e); (g) detecting movement of the ferromagnetic object in the chamber; (h) determining whether the detected movement of the first ferromagnetic meets a predetermined ferromagnetic threshold for clot weakening; and (i) repeating steps (f)-(h) until the detected movement of the ferromagnetic meets the predetermined ferromagnetic threshold for clot weakening.

An eleventh aspect is a method of the tenth aspect, further comprising: (j) inputting decreased energy relative to step (e) to cause the ferromagnetic object to move or attempt to cause the ferromagnetic object to move in the chamber; (k) detecting movement of the ferromagnetic object in the chamber; (l) determining whether the detected movement of the ferromagnetic object returns to the initial object travel distance or velocity; (m) inputting energy at the same level as input in step (i) to cause the ferromagnetic object to move or attempt to cause the ferromagnetic object to move in the chamber if the detected movement of the ferromagnetic object does not return to the initial object travel distance or velocity; and (n) repeating step (j) to (m) until energy is reduced to the test initial level.

A twelfth is a system for analyzing clotting of blood, wherein the system is configured to carry out the method of any of aspects 1-11 or 35-36.

A thirteenth aspect is a system according to aspect 12, comprising: (i) a chamber for housing blood; (ii) an object moveable within the chamber when blood is present in the chamber; (iii) a detector configured to detect the position of the object within the chamber; and (iv) electronics operably coupled to the detector and to the object such that the electronics are configured to control movement of the object within the chamber, wherein the electronics, based on data received from the detector, are further configured to determine a parameter associated with clot strength.

A fourteenth aspect is a non-transitory computer-readable medium programmed with instructions that, when executed, cause a system to carry out the method any of aspects 1-11 or 35-36.

A fifteenth aspect is a method carried out by a system configured to analyze blood clotting, comprising: (i) causing an object to move in a chamber housing blood; (ii) detecting movement of the object in the chamber in a first period of time and detecting movement of the object in the first chamber in a second period of time, wherein the second period of time is after the first period of time; (iii) determining whether the detected movement of the object in the first period of time is indicative of clotting; (iv) determining whether the detected movement of the object in the second period of time is indicative of clotting; (v) determining elapsed time between the first period of time and the second period of time; and (vi) correlating strength of blood clotting to the length of the elapsed time if the detected movement of the object in the first period of time is determined to be indicative of clotting and if the detected movement of the object in the second period of time is not indicative of clotting.

A sixteenth aspect is a method of the fifteenth aspect, wherein determining whether the detected movement of the object in the second period of time is indicative of clotting comprises determining whether the detected movement of the object in the second period of time is greater than the detected movement of the object in the first period of time.

A seventeenth aspect is a system for analyzing clotting of blood, wherein the system is configured to carry out the method of aspect 15 or aspect 16.

An eighteenth aspect is a system according to aspect 17, comprising: (i) a chamber for housing blood; (ii) an object moveable within the chamber when blood is present in the chamber; (iii) a detector configured to detect the position of the object within the chamber; and (iv) electronics operably coupled to the detector and to the object such that the electronics are configured to control movement of the object within the chamber, wherein the electronics, based on data received from the detector, are further configured to determine a parameter associated with clot strength.

A nineteenth aspect is a non-transitory computer-readable medium programmed with instructions that, when executed, cause a system to carry out the method of aspect 15 or aspect 16.

A twentieth aspect is a method carried out by a system configured to analyze blood clotting, comprising: (a) attempting to cause an object to move in a chamber housing blood in a first predetermined time after the blood has clotted; (b) detecting movement of the object in the chamber after attempting to cause the first object to move; (c) determining whether the detected movement of the object meets or exceeds a predetermined threshold; (d) attempting to cause the object to move in the chamber housing the blood at a subsequent predetermined time if the detected movement of the first object is determined to not meet or exceed the threshold in step (c); (e) repeating steps (c) and (d) until the detected movement of the object is determined to meet or exceed the predetermined threshold; until steps (c) and (d) are repeated a predetermined number of times; or until a passage of a predetermined length of time; (f) determining the length of time from the first predetermined time in step (a) until a conditions of step (c) or step (e) is met; and (g) correlating the length of time determined in step (f) to the strength of the clot.

A twenty-first aspect is a system for analyzing clotting of blood, wherein the system is configured to carry out the method of aspect 20.

A twenty-second aspect is a system according to aspect 21, comprising: (i) a chamber for housing blood; (ii) an object moveable within the chamber when blood is present in the chamber; (iii) a detector configured to detect the position of the object within the chamber; and (iv) electronics operably coupled to the detector and to the object such that the electronics are configured to control movement of the object within the chamber, wherein the electronics, based on data received from the detector, are further configured to determine a parameter associated with clot strength.

A twenty-third aspect is a non-transitory computer-readable medium programmed with instructions that, when executed, cause a system to carry out the method of aspect 20.

A twenty-fourth aspect is a method carried out by a system configured to analyze blood clotting comprising: (i) expending energy to cause, or attempt to cause, an object to move in a chamber housing blood that has clotted; (ii) detecting the amount of energy expended in causing, or attempting to cause, the object to move; and (iii) correlating the amount of energy expended with strength of clotting of the blood.

A twenty-fifth aspect is a method of aspect 24, further comprising (i) detecting movement of the object in the chamber; and (ii) correlating the detected movement of first object with the clotting strength of the blood.

A twenty-sixth aspect is a method of aspect 25, wherein expending energy to cause, or attempt to cause, the object to move in the chamber housing blood comprises expending energy in a first period of time to cause, or attempt to cause, the object to move a first time and expending energy in a second period of time to cause, or attempt to cause, the object to move a second time, wherein detecting the movement of the first object in the first chamber comprises detecting a rate of movement in the first period of time and detecting a rate of movement in the second period of time, and wherein the method further comprises: determining whether the rate of movement of the object in the first period of time is below a threshold vale indicative of clotting, wherein the energy expended in the second period of time is configured to cause the object to move more slowly than the energy expended in the first period of time if the rate of movement of the object at the first period of time is determined to be below a threshold value indicative of clotting.

A twenty-seventh aspect is a method of aspect 24, wherein expending energy to cause, or attempt to cause, the object to move in the chamber housing blood comprises expending energy in a first period of time to cause, or attempt to cause, the object to move a first time and expending energy in a second period of time to cause, or attempt to cause, the object to move a second time, wherein detecting movement of the object in the chamber comprises detecting movement in the first period of time and detecting movement in the second period of time, and wherein the method further comprises: determining whether the movement of the object in the first period of time is below a threshold value indicative of clotting, allowing a predetermined length of time to elapse before expending energy in the second period of time to cause, or attempt to cause the object to move, determining whether the movement of the object at the second period of time is below a threshold value indicative of clotting, and wherein correlating the amount of energy expended with strength of clotting of the blood comprises comparing the amount of energy expended in the first period of time to the amount of energy expended in the second period of time if it is determined that the movement of the object in the first period of time and in the second period of time are below a threshold values indicative of clotting.

A twenty-eighth aspect is a system for analyzing clotting of blood, wherein the system is configured to carry out the method of aspect 27.

A twenty-ninth aspect is a system according to aspect 28, comprising: (i) a first chamber for housing blood; (ii) a first object moveable within the chamber when blood is present in the chamber; (iii) an energy source operably coupled to the first moveable object; and (iv) electronics operably coupled to the energy source to control movement of the first object within the first chamber, wherein the electronics are further configured to determine a parameter associated with clot strength based on a parameter associated with control of the energy source.

A thirtieth aspect is a non-transitory computer-readable medium programmed with instructions that, when executed, cause a system to carry out the method of aspect 27.

A thirty-first aspect is a method carried out by a system configured to analyze blood clotting, comprising: (a) applying energy configured to cause ant object to move in a chamber housing blood that has clotted; (b) detecting movement of the object in the chamber during or after the application of energy; (c) determining whether the detected movement of the object meets or exceeds a predetermined threshold; (d) applying additional energy configured to cause the object to move if the detected movement of the object is determined not to meet or exceed the threshold in step (c); (e) repeating steps (c) and (d) until the detected movement of the object is determined to meet or exceed the predetermined threshold or until predetermined energy threshold is met or exceeded; and (f) correlating the amount of energy applied to attempt to cause, or cause, the object to move with the strength of the clot.

A thirty-second aspect is a system for analyzing clotting of blood, wherein the system is configured to carry out the method of aspect 31.

A thirty-third aspect is a system according to aspect 32, comprising: (i) a first chamber for housing blood; (ii) a first object moveable within the chamber when blood is present in the chamber; (iii) an energy source operably coupled to the first moveable object; and (iv) electronics operably coupled to the energy source to control movement of the first object within the first chamber, wherein the electronics are further configured to determine a parameter associated with clot strength based on a parameter associated with control of the energy source.

A thirty-fourth aspect is a non-transitory computer-readable medium programmed with instructions that, when executed, cause a system to carry out the method of aspect 31.

A thirty fifth aspect is a method of any of aspects 1-8, further comprising: (a) causing a second ferromagnetic object to move in a second chamber housing blood; (b) detecting movement of the second ferromagnetic object in the second chamber; (c) determining whether the detected movement of the second ferromagnetic object meets a threshold indicative of clotting; and (d) repeating steps (a)-(c) until the detected movement of the second ferromagnetic object meets the threshold indicative of clot initiation, wherein causing the first ferromagnetic object to move in the first chamber housing blood after clot initiation has been detected comprises causing the first ferromagenetic object to move after the detected movement of the second ferromagenetic object meets the threshold indicative of clot initiation.

A thirty sixth aspect is a method of any of aspects 1-8, further comprising (a) causing the ferromagenetic object to move in the first chamber; (b) detecting movement of the first ferromagnetic object in the first chamber; (c) determining whether the detected movement of the first ferromagnetic object meets a threshold indicative of clotting; and (d) repeating steps (a)-(c) until the detected movement of the first ferromagenetic object meets the threshold indicative of clot initiation, wherein the first object is biased towards the bottom of the chamber by a biasing member such that upon clot formation, the clot forms on top of or around the object.

Thus, embodiments of APPARATUS AND METHOD FOR ANALYZING BLOOD CLOTTING are disclosed. One skilled in the art will appreciate that the leads, devices such as signal generators, systems and methods described herein can be practiced with embodiments other than those disclosed. The disclosed embodiments are presented for purposes of illustration and not limitation. One will also understand that components of the leads depicted and described with regard the figures and embodiments herein may be interchangeable.

The invention claimed is:

1. A method carried out by a system configured to analyze blood clotting, comprising:
   causing a first ferromagnetic object to move in a first chamber housing blood after clot initiation has been detected, wherein causing the first object to move in the first chamber comprises causing the first object to move in the first chamber against the force of gravity, and wherein detecting movement of the first object in the first chamber comprises detecting movement of the first object due to the force of gravity;
   detecting movement of the first ferromagnetic object in the first chamber; and
   correlating the detected movement of the first ferromagnetic object in the first chamber with strength of clotting of the blood.

2. The method of claim 1,
   wherein detecting movement of the first object in the first chamber comprises detecting movement in a first period of time and detecting movement in a second period of time, and
   wherein correlating detected movement of the first object in the first chamber with the strength of clotting comprises comparing movement of the first object in the first chamber in the first period of time to movement of the object in the first chamber in the second period of time.

3. The method of claim 2, wherein correlating movement of the first object in the first chamber with the strength of clotting comprises determining a rate of change in velocity of the first object between the first period of time and the second period of time and correlating the rate of change in velocity with the strength of clotting.

4. The method of claim 2, wherein correlating movement of the first object in the first chamber with the strength of clotting comprises determining a magnitude in the difference between movement of the object in the first chamber in the first period of time and movement of the first object in the first chamber in the second period of time and correlating the magnitude with the strength of clotting.

5. The method of claim 1, further comprising detecting clot initiation.

6. The method of claim 5, wherein detecting clot initiation comprises:
   causing the first ferromagnetic object to move in the first chamber housing the blood;
   detecting movement of the first ferromagnetic object in the first chamber; and
   determining whether the detected movement has decreased below a predetermined threshold,
   wherein, if the detected movement has decreased below the predetermined threshold, clot initiation is detected.

7. A system for analyzing clotting of blood, wherein the system is configured to carry out the method of claim 1.

8. A system according to claim 7, comprising:
   a chamber for housing blood;
   an object moveable within the chamber when blood is present in the chamber;
   a detector configured to detect the position of the object within the chamber; and
   electronics operably coupled to the detector and to the object such that the electronics are configured to control movement of the object within the chamber,
   wherein the electronics, based on data received from the detector, are further configured to determine a parameter associated with clot strength.

9. A non-transitory computer-readable medium programmed with instructions that, when executed, cause a system to carry out the method of claim 1.

10. A method carried out by an apparatus or system configured to analyze blood clotting, comprising:
    (a) inputting energy to cause a ferromagnetic object to move in a chamber housing blood;
    (b) detecting movement of the ferromagnetic object in the chamber and determining an initial object travel distance or velocity;
    (c) determining whether the detected movement of the ferromagnetic object meets a predetermined ferromagnetic object travel distance threshold or velocity threshold for clot formation;
    (d) inputting increased energy relative to step (a) to cause the ferromagnetic object to move the initial travel distance or velocity; and
    (e) repeating steps (c)-(d) until the detected movement of the ferromagnetic object in the chamber meets the predetermined ferromagnetic object travel distance or velocity threshold for clotting or until a predetermined energy threshold is met or exceeded, the method further comprising:
    (f) applying energy to cause the ferromagnetic object to move or attempt to move at a level of energy applied at step (e);
    (g) detecting movement of the ferromagnetic object in the chamber;
    (h) determining whether the detected movement of the ferromagnetic object meets a predetermined ferromagnetic threshold for clot weakening; and
    (i) repeating steps (f)-(h) until the detected movement of the ferromagnetic object meets the predetermined ferromagnetic threshold for clot weakening.

11. The method of claim 10, further comprising:
    (j) inputting decreased energy relative to step (e) to cause the ferromagnetic object to move or attempt to cause the ferromagnetic object to move in the chamber;
    (k) detecting movement of the ferromagnetic object in the chamber;
    (l) determining whether the detected movement of the ferromagnetic object returns to the initial object travel distance or velocity;

(m) inputting energy at the same level as input in step (i) to cause the ferromagnetic object to move or attempt to cause the ferromagnetic object to move in the chamber if the detected movement of the ferromagnetic object does not return to the initial object travel distance or velocity; and (n) repeating step (j) to (m) until energy is reduced to a test initial level.

12. A method carried out by a system configured to analyze blood clotting, comprising:

causing an object to move in a chamber housing blood;

detecting movement of the object in the chamber in a first period of time and detecting movement of the object in the first chamber in a second period of time, wherein the second period of time is after the first period of time;

determining whether the detected movement of the object in the first period of time is indicative of clotting;

determining whether the detected movement of the object in the second period of time is indicative of clotting by determining whether the detected movement of the object in the second period of time is less than the detected movement of the object in the first period of time;

determining elapsed time between the first period of time and the second period of time; and correlating strength of blood clotting to the length of the elapsed time if the detected movement of the object in the first period of time is determined to be indicative of clotting and if the detected movement of the object in the second period of time is not indicative of clotting.

13. A system for analyzing clotting of blood, wherein the system is configured to carry out the method of claim 12.

14. A system according to claim 13, comprising:

a chamber for housing blood;

an object moveable within the chamber when blood is present in the chamber;

a detector configured to detect the position of the object within the chamber; and electronics operably coupled to the detector and to the object such that the electronics are configured to control movement of the object within the chamber, wherein the electronics, based on data received from the detector, are further configured to determine a parameter associated with clot strength.

15. A non-transitory computer-readable medium programmed with instructions that, when executed, cause a system to carry out the method of claim 12.

16. A method carried out by a system configured to analyze blood clotting comprising:

expending energy to cause, or attempt to cause, an object to move in a chamber housing blood by expending energy in a first period of time to cause, or attempt to cause, the object to move a first time and expending energy in a second period of time to cause, or attempt to cause, the object to move a second time;

detecting the amount of energy expended in causing, or attempting to cause, the object to move;

correlating the amount of energy expended with strength of clotting of the blood;

detecting movement of the object in the chamber by detecting a rate of movement in the first period of time and detecting a rate of movement in the second period of time; and correlating the detected movement of the object with the clotting strength of the blood, wherein the method further comprises;

determining whether the rate of movement of the object in the first period of time is below a threshold vale indicative of clotting, wherein the energy expended in the second period of time is configured to cause the object to move more slowly than the energy expended in the first period of time if the rate of movement of the object at the first period of time is determined to be below a threshold value indicative of clotting.

17. The method of claim 16, wherein the method further comprises allowing a predetermined length of time to elapse before expending energy in the second period of time to cause, or attempt to cause the object to move.

18. A system for analyzing clotting of blood, wherein the system is configured to carry out the method of claim 17.

19. A system according to claim 18, comprising:

a first chamber for housing blood;

a first object moveable within the chamber when blood is present in the chamber;

an energy source operably coupled to the first moveable object; and electronics operably coupled to the energy source to control movement of the first object within the first chamber, wherein the electronics are further configured to determine a parameter associated with clot strength based on a parameter associated with control of the energy source.

20. A non-transitory computer-readable medium programmed with instructions that, when executed, cause a system to carry out the method of claim 17.

21. The method of claim 16 wherein correlating the amount of energy expended with strength of clotting of the blood comprises comparing the amount of energy expended in the first period of time to the amount of energy expended in the second period of time if it is determined that the movement of the object in the first period of time and in the second period of time are below a threshold value indicative of clotting.

22. A method carried out by a system configured to analyze blood clotting, comprising:

causing a first ferromagnetic object to move in a first chamber housing blood after clot initiation has been detected, detecting movement of the first ferromagnetic object in the first chamber; and correlating the detected movement of the first ferromagnetic object in the first chamber with strength of clotting of the blood, the method further comprising:

(a) causing a second ferromagenetic object to move in a second chamber housing blood;

(b) detecting movement of the second ferromagnetic object in the second chamber;

(c) determining whether the detected movement of the second ferromagnetic object meets a threshold indicative of clotting; and (d) repeating steps (a)-(c) until the detected movement of the second ferromagenetic object meets the threshold indicative of clotting, wherein causing the first ferromagnetic object to move in the first chamber housing blood after clot initiation has been detected comprises causing the first ferromagenetic object to move after the detected movement of the second ferromagenetic object meets the threshold indicative of clotting.

23. A method carried out by a system configured to analyze blood clotting, comprising:

causing a first ferromagnetic object to move in a first chamber housing blood after clot initiation has been detected;

detecting movement of the first ferromagnetic object in the first chamber; and correlating the detected movement of the first ferromagnetic object in the first chamber with strength of clotting of the blood, the method further comprising
(a) causing the ferromagenetic object to move in the first chamber;
(b) detecting movement of the first ferromagnetic object in the first chamber;
(c) determining whether the detected movement of the first ferromagnetic object meets a threshold indicative of clotting; and
(d) repeating steps (a)-(c) until the detected movement of the first ferromagenetic object meets the threshold indicative of clotting,
wherein the first object is biased towards the bottom of the chamber by a biasing member such that upon clot formation, the clot forms on top of or around the object.

24. A method carried out by a system configured to analyze blood clotting, comprising:

causing a first ferromagnetic object to move in a first chamber housing blood after clot initiation has been detected, wherein causing the first object to move in the first chamber comprises causing the first object to move in the first chamber against the force of gravity, and wherein detecting movement of the first object in the first chamber comprises detecting movement of the first object against the force of gravity;

detecting movement of the first ferromagnetic object in the first chamber; and correlating the detected movement of the first ferromagnetic object in the first chamber with strength of clotting of the blood.

* * * * *

UNITED STATES PATENT AND TRADEMARK OFFICE
CERTIFICATE OF CORRECTION

PATENT NO. : 8,921,115 B2  Page 1 of 1
APPLICATION NO. : 13/788283
DATED : December 30, 2014
INVENTOR(S) : Yuan et al.

It is certified that error appears in the above-identified patent and that said Letters Patent is hereby corrected as shown below:

In the Claims

In column 19, lines 7-8, claim 11 "... (n) repeating step (j) to (m) until energy is reduced to a test initial level. ..." should read -- "... (n) repeating steps (j) to (m) until energy is reduced to a test initial level. ..." --

In column 20, lines 1-3, claim 16 "... determining whether the rate of movement of the object in the first period of time is below a threshold vale indicative of clotting. ..."
should read -- "... determining whether the rate of movement of the object in the first period of time is below a threshold value indicative of clotting. ..." --

In column 21, lines 3-5, claim 23 "... correlating the detected movement of the first ferromagnetic object in the first chamber with strength of clotting of the blood, the method further comprising ..." should read -- "... correlating the detected movement of the first ferromagnetic object in the first chamber with strength of clotting of the blood, the method further comprising: ..." --

Signed and Sealed this
Twenty-sixth Day of April, 2016

Michelle K. Lee
*Director of the United States Patent and Trademark Office*